United States Patent
Uemura et al.

(10) Patent No.: US 9,902,013 B2
(45) Date of Patent: Feb. 27, 2018

(54) EDGED TOOL, METHOD OF MANUFACTURING THE SAME, AND PLASMA DEVICE FOR MANUFACTURING THE SAME

(71) Applicants: SHINMAYWA INDUSTRIES, LTD., Takarazuka-shi, Hyogo (JP); KAI R&D CENTER CO., LTD, Seki-shi, Gifu (JP)

(72) Inventors: Kensuke Uemura, Takarazuka (JP); G. Alexey Remnev, Takarazuka (JP); V. Konstantin Shalnov, Takarazuka (JP); Tsukasa Tamaoki, Seki (JP)

(73) Assignees: SHINMAYWA INDUSTRIES, LTD., Takarazuka (JP); KAI R&D CENTER CO., LTD., Seki (JP)

( * ) Notice: Subject to any disclaimer, the term of this patent is extended or adjusted under 35 U.S.C. 154(b) by 7 days.

(21) Appl. No.: 14/394,890

(22) PCT Filed: Apr. 11, 2013

(86) PCT No.: PCT/JP2013/060913
§ 371 (c)(1),
(2) Date: Oct. 16, 2014

(87) PCT Pub. No.: WO2013/157473
PCT Pub. Date: Oct. 24, 2013

(65) Prior Publication Data
US 2015/0096423 A1    Apr. 9, 2015

(30) Foreign Application Priority Data
Apr. 18, 2012 (JP) ................................ 2012-094536

(51) Int. Cl.
B23K 10/00    (2006.01)
A61B 17/3211    (2006.01)
(Continued)

(52) U.S. Cl.
CPC .......... *B23K 10/00* (2013.01); *A61B 17/3211* (2013.01); *B26B 21/4068* (2013.01);
(Continued)

(58) Field of Classification Search
CPC ..... Y10T 83/9495; Y10T 83/04; B23K 10/00; A61B 17/3211; A61B 2017/00526;
(Continued)

(56) References Cited

U.S. PATENT DOCUMENTS 2,566,112 A * 8/1951 Barnard .................... B26B 9/00
30/348
4,495,698 A * 1/1985 Gerber, Jr. ................ B26B 9/00
30/357
(Continued)

FOREIGN PATENT DOCUMENTS

EP    0194652 A1    9/1986
JP    S61210179 A    9/1986
(Continued)

OTHER PUBLICATIONS

Nov. 17, 2015 Supplementary Search Report issued in European Patent Application No. 13 77 7510.
(Continued)

Primary Examiner — Phong Nguyen
(74) Attorney, Agent, or Firm — Oliff PLC (57) ABSTRACT

The invention addresses the problem of providing an edged tool such as a surgical blade or a razor blade that is durable and sharp, and a manufacturing method therefor. The problem is solved by an edged tool manufacturing method provided with a process of treating a metal base material, which has a machined surface obtained by machining, using a plasma generated in an atmosphere filled with a mixed gas having a main gas and a reaction gas as the main components.

4 Claims, 4 Drawing Sheets

(51) Int. Cl.
*C23F 4/00* (2006.01)
*B26B 21/56* (2006.01)
*B26B 21/40* (2006.01)
*C23C 8/38* (2006.01)
*A61B 17/00* (2006.01)

(52) U.S. Cl.
CPC ............... *B26B 21/56* (2013.01); *C23C 8/38* (2013.01); *C23F 4/00* (2013.01); *A61B 2017/00526* (2013.01); *F04C 2270/041* (2013.01); *Y10T 83/9495* (2015.04)

(58) Field of Classification Search
CPC ..... B26B 21/4068; B26B 21/56; C23C 83/38; C23F 4/00
See application file for complete search history.

(56) References Cited

U.S. PATENT DOCUMENTS

| | | | |
|---|---|---|---|
| 5,032,243 A | 7/1991 | Bache et al. | |
| 5,477,616 A * | 12/1995 | Williams | B26B 9/00 30/350 |
| 7,228,633 B2 * | 6/2007 | Ryan | F41B 13/02 30/346 |
| 2002/0017455 A1 | 2/2002 | Kirkpatrick et al. | |
| 2004/0187314 A1 * | 9/2004 | Johnson | B26B 9/02 30/162 |
| 2006/0157159 A1 * | 7/2006 | Yeung | A61L 27/06 148/239 |
| 2008/0016704 A1 | 1/2008 | Haneda | |
| 2010/0071216 A1 | 3/2010 | Novak | |
| 2010/0288097 A1 | 11/2010 | Uemura et al. | |
| 2011/0120973 A1 | 5/2011 | Zhuk et al. | |
| 2011/0244142 A1 * | 10/2011 | Cheng | C23C 16/26 427/569 |
| 2013/0213575 A1 * | 8/2013 | Kim | H05H 1/46 156/345.44 |
| 2016/0015908 A1 | 1/2016 | Uemura et al. | |

FOREIGN PATENT DOCUMENTS

| | | |
|---|---|---|
| JP | H0317269 A | 1/1991 |
| JP | H03-501458 A | 4/1991 |
| JP | H042666 B2 | 1/1992 |
| JP | H0623157 A | 2/1994 |
| JP | 2779453 B2 | 7/1998 |
| JP | 2000-073156 A | 3/2000 |
| JP | 2003105478 A | 4/2003 |
| JP | 3451140 B2 | 9/2003 |
| JP | 2004217489 A | 8/2004 |
| JP | 2004-290410 A | 10/2004 |
| JP | 2004298562 A | 10/2004 |
| JP | 2005074221 A | 3/2005 |
| JP | 2007-227149 A | 9/2007 |
| JP | 2009153877 A | 7/2009 |
| JP | 5354827 B1 | 11/2013 |
| WO | 9003455 A1 | 4/1990 |

OTHER PUBLICATIONS

Jun. 4, 2013 International Search Report issued in International Application No. PCT/JP2013/060913.
Jun. 4, 2013 Written Opinion of the International Searching Authority issued in International Application No. PCT/JP2013/060913.
Mar. 22, 2016 Office Action issued in Japanese Patent Application No. 2012-094536.

* cited by examiner

EDGED TOOL, METHOD OF MANUFACTURING THE SAME, AND PLASMA DEVICE FOR MANUFACTURING THE SAME

TECHNICAL FIELD

The present invention relates to an edged tool such as surgical blade, shaving razor and so forth, a method of manufacturing the same, and a plasma device for manufacturing the same.

BACKGROUND ART

Edged tools represented by surgical blade (scalpel, etc.) and shaving razor preferably have high sharpness of their edges.

The following proposals have been made on these sorts of edged tools.

For example, Patent Literature 1 describes a blade member which includes edges of a group of blades subjected to ion beam treatment using a plasma ion gun in a vacuum chamber, in which argon is used as a medium, wherein the pressure of the argon gas is 0.1 to 1 Pa, a bias voltage applied to the blade group is 0.1 to 1000V, and the processing time is 5 to 300 minutes. According to the description, an edged tool with enhanced sharpness and clean cuttability was successfully provided by improving a processing technology based on ion beam processing.

In other example, Patent Literature 2 describes a method of surface modification of blade edges of sharp edge tools, wherein the method includes subjecting sharp metal edged tools to vacuum evaporation, while applying in vacuo negative voltage to the blade edges of sharp metal edged tools to cause ion implantation of anion on the surface of the blade edge. According to the description, such method successfully improves mechanical properties of the surgical layer of the blade edges.

In still other example, Patent Literature 3 proposes a method of shaping or reshaping a blade edge by removing a blade material from both sides of the blade edge, by sputtering using argon ion. It is also described that the shape of blade edge as a result of ion bombardment is given by W=ad$^n$ (where, W represents the thickness of the blade edge measured at distance d away from the end of blade, and a and n are constants).

Again in still other example, Patent Literature 4 describes a technique of increasing hardness of an edged tool by forming on the surface thereof a hard layer composed of an intermetallic compound by plasma ion nitriding, or by forming on the surface a diamond-like carbon film, to thereby suppress wearing, and to prevent dulling.

CITATION LIST

Patent Literature

Patent Literature 1: JP-A-2009-153877
Patent Literature 2: JP-B-H04-2666
Patent Literature 3: Examined Japanese Patent No. 2779453
Patent Literature 4: JP-A-2004-298562

SUMMARY OF THE INVENTION

Technical Problem

The edged tool is, however, desired to have still better cuttability, while keeping the durability.

It is therefore an object of the present invention to provide an edged tool having still better cuttability, despite an equivalent level of durability as compared with the conventional edged tools, a method of manufacturing the same, and a plasma device for manufacturing the same.

Solution to Problem

Aiming at solving the problems described above, the inventors accomplished the present invention after our thorough investigations.

The present invention includes items (1) to (9) below.

(1) A method of manufacturing an edged tool, the method including treating a metal base, having a machined surface obtained by machining, with a plasma generated in an atmosphere filled with a mixed gas mainly composed of a major gas and a reactive gas.

(2) The method of manufacturing an edged tool described in (1), wherein the ratio (AGP/MGP) of partial pressure of reactive gas (AGP) and partial pressure of major gas (MGP) in the mixed gas is 0.001 to 0.1.

(3) The method of manufacturing an edged tool described in (1) or (2), wherein the partial pressure of major gas (MGP) in the mixed gas is 0.01 to 10 Pa, and the partial pressure of reactive gas (AGP) is 0.001 Pa or higher.

(4) The method of manufacturing an edged tool of any one described in (1) to (3), wherein the major gas is nitrogen, and the reactive gas is oxygen.

(5) The method of manufacturing an edged tool of any one described in (1) to (4), wherein the metal base is a blade base formed by machining a plate-like blade forming member at the belly-side end from both sides in the thickness direction, so as to give two machined surfaces which come apart in the direction from the edge towards the spine, while forming in between a predetermined sharpening angle.

(6) An edged tool obtained by the method of manufacturing described in any one described in (1) to (5).

(7) The edged tool described in (6), wherein the machined surface has formed therein a concave surface, with a predetermined radius of curvature, which caves inwardly within range H originated from the edge end towards the spine.

(8) The edged tool described in (7), wherein the radius of curvature of the concave surface is 30 to 2500 nm, and the range H is 5 to 300 nm.

(9) A plasma device suitable for implementing the manufacturing method described in any one described in (1) to (5), the plasma device including a vacuum chamber, a gas feeding unit which introduces the mixed gas into the vacuum chamber, a holder which holds the metal base placed in the vacuum chamber and a filament disposed face-to-face therewith, and a power source for filament which feeds current to the filament.

ADVANTAGEOUS EFFECTS OF INVENTION

According to the present invention, durable edged tool having a good level of cuttability, a method of manufacturing such edged tool, and a plasma device for manufacturing such edged tool may be provided.

DESCRIPTION OF EMBODIMENTS

The present invention will be explained.

The present invention relates to a method of manufacturing an edged tool, which includes treating a metal base, having a machined surface obtained by machining, with a plasma generated in an atmosphere filled with a mixed gas mainly composed of a major gas and a reactive gas.

Such method of manufacturing is also referred to as "the manufacturing method of this invention" hereinafter.

The edged tool obtainable by the manufacturing method of this invention is also referred to as "the edged tool of this invention" hereinafter.

<Metal Base>

First, the metal base used in the manufacturing method of this invention will be explained.

Figure 1:
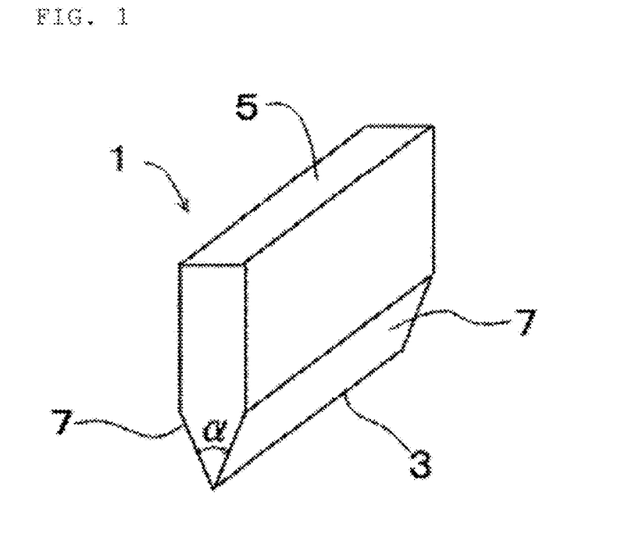
FIG. 1 is a schematic drawing exemplifying a shape of a metal base (blade base) usable for the present invention.

In the manufacturing method of this invention, the metal base is not specifically limited so long as it has a machined surface obtained by machining, and so long as it is usable to give edged tools such as surgical blade (scalpel, etc.), shaving razor and so forth. As illustrated in FIG. 1, the metal base is preferably a blade base 1 formed by machining a plate-like blade forming member at the belly-side end from both sides in the thickness direction, so as to give two machined surfaces 7 which come apart in the direction from the edge 3 towards the spine (back end 5), while forming in between a predetermined sharpening angle α. A more better embodiment and a method of manufacturing will be described later.

Size and material of the metal base are not specifically limited so long as the metal base is usable for general surgical blade, shaving razor or the like. A plate-like material composed of stainless steel, for example, is usable.

The machined surface of the metal base is preferably obtained by machining. The machining is exemplified by grinding, drawing and polishing (blasting, stropping, etc.). It is preferable to combine two or more sorts of machining. More specifically, grinding is preferably followed by polishing.

A preferable embodiment of the metal base in the manufacturing method of this invention will be explained referring to FIG. 2. The metal base in the manufacturing method of this invention is preferably a blade base illustrated in FIG. 2.

Figure 2:
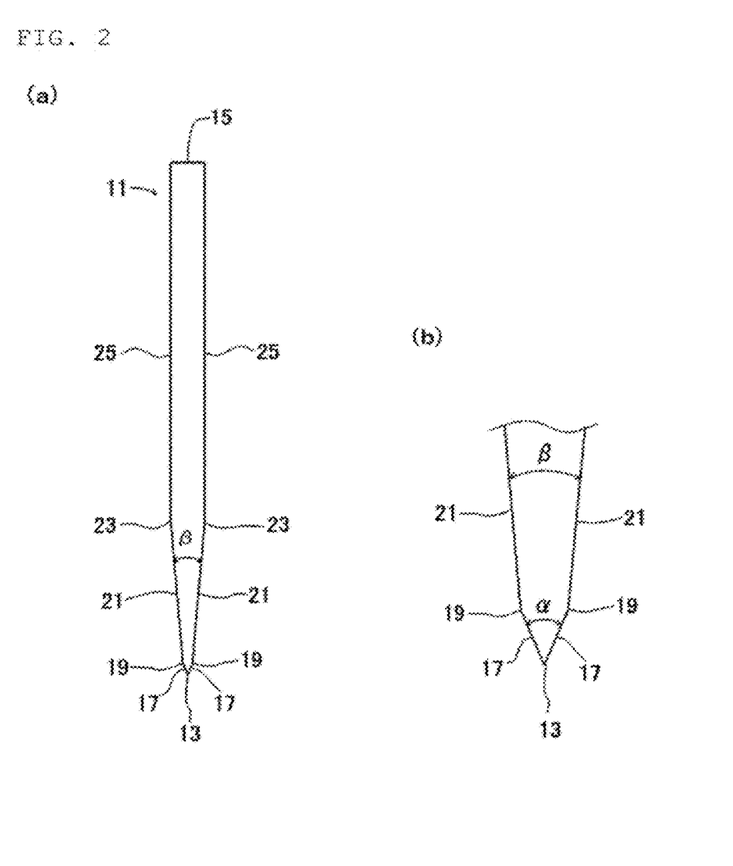
FIG. 2 is another schematic drawing exemplifying a shape of a metal base (blade base) usable for the present invention.

FIG. 2(a) is a schematic cross sectional view of the blade base, and FIG. 2(b) is an enlarged view of the edge and a periphery thereof illustrated in FIG. 2(a).

A blade base 11 illustrated in FIG. 2 is formed by machining a plate-like blade forming member at the belly-side end (edge 13 side) from both sides in the thickness direction, so as to give two machined surfaces 17 which come apart in the direction from the edge 13 towards the spine (back end 15 side), while forming in between a predetermined sharpening angle α, further so as to give two apical surfaces 21 which extend respectively from two machined surfaces 17 beyond a first boundary 19 towards the spine (back end 15 side) while forming in between a predetermined apical angle β, and still further so as to give two side faces 25 which extend respectively from two apical surfaces 21 beyond a second boundary 23 towards the spine (back end 15 side).

With the metal base given as the blade base 11 of this embodiment, the edged tool of this invention will preferably have an improved sharpness.

While a method of manufacturing the blade base 11 of this preferable embodiments is not specifically limited, the blade base 11 is preferably manufactured according to a method explained below referring to FIG. 3.

Figure 3:
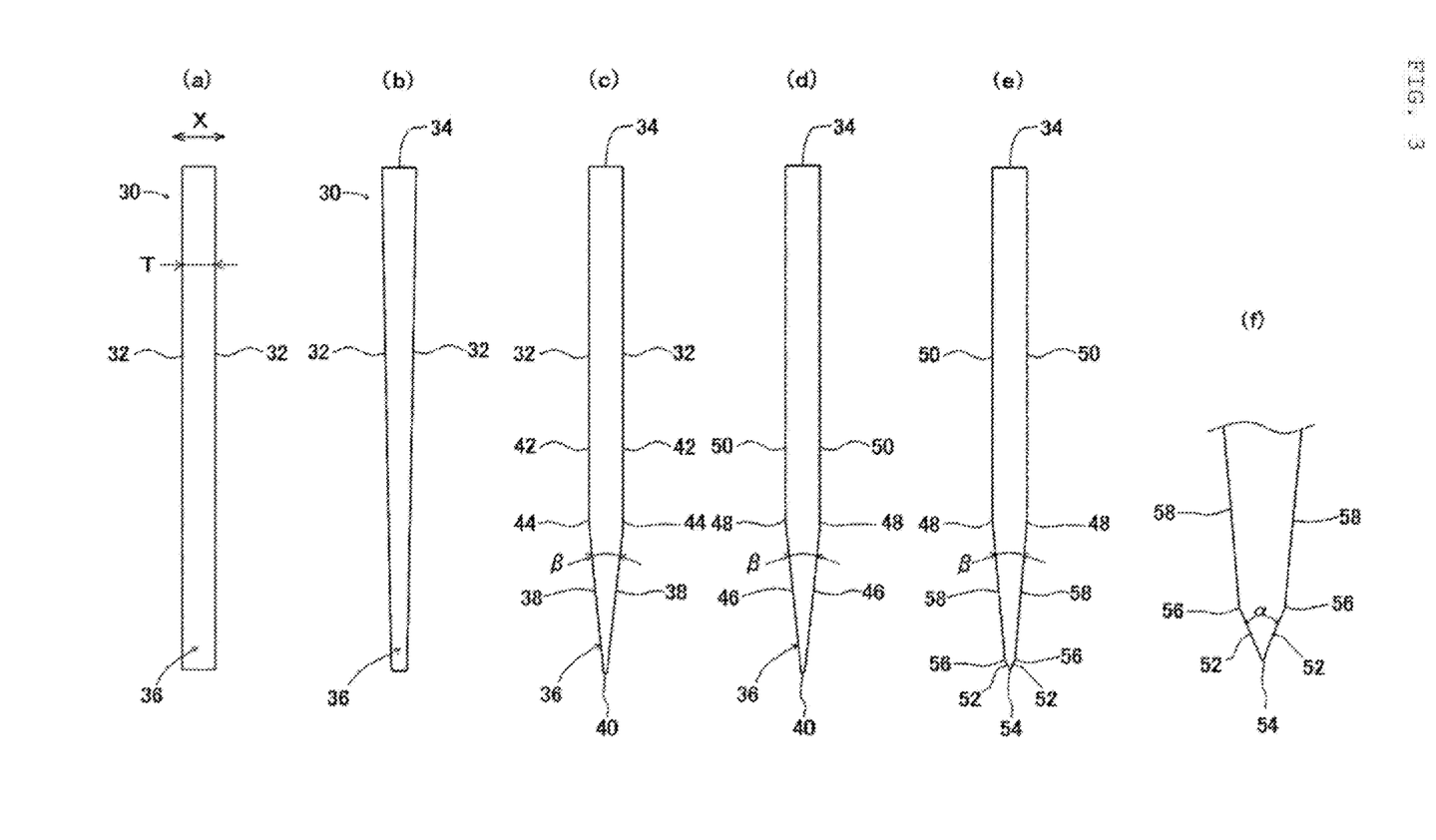
FIG. 3 is a drawing explaining a method of manufacturing a metal base usable for the present invention, in an illustrative manner.

First, as illustrated in FIG. 3(a), a plate-like blade forming member 30, formed with a predetermined shape and with thickness T, is ground from both side faces 32 which align nearly parallel to each other in the thickness direction X. As a result of grinding, as illustrated in FIG. 3(b), both side faces 32 of the blade forming member 30 are inclined, so that the thickness of the blade forming member 30 becomes thinner from the back end 34 side towards the belly-side end 36.

Next, both side faces 32 of the blade forming member 30 illustrated in FIG. 3(b) are ground on the belly-side end 36 thereof. As a result of grinding, as illustrated in FIG. 3(c), two apical ground surfaces 38 are formed so as to obliquely extend from the belly-side end 36 towards the spine, while forming in between a predetermined apical angle β, up to a predetermined range from the edge end 40. On both side faces 32 of the blade forming member 30, ground side faces 42 which lie between the apical ground surfaces 33 and the back end 34 are left as they are illustrated in FIG. 3(b).

Next, assuming now the boundaries between the apical ground surfaces 38 and the ground side faces 42 as boundaries 44, the apical ground surfaces 38, the boundaries 44, and the ground side faces 42 which extend from the boundaries 44 are polished. As a result of polishing, as illustrated in FIG. 3(d), two apical polished surfaces 46 are formed so as to obliquely extend from the edge end 40 towards the spine, while forming in between a predetermined apical angle β, and side polished surfaces 50 are formed so as to extend from the apical polished surfaces 46 beyond the boundaries 48 towards the spine.

Next, the apical polished surfaces 46 are machined to give an edge at the edge end 40. More specifically, as illustrated in FIG. 3(e) and FIG. 3(f), two machined surfaces 52 are formed so as to obliquely extend towards the spine, while forming in between a predetermined sharpening angle α, within a predetermined region which originates from the edge end 54. Also apical surfaces 58 are formed so as to obliquely extend from these two machined surfaces 52 beyond the boundaries 56 towards the spine, while forming in between a predetermined apical angle β.

<Plasma Treatment>

Next, plasma treatment in the manufacturing method of this invention will be explained.

In the manufacturing method of this invention, at least the machined surfaces of the metal base are subjected to plasma treatment.

The plasma treatment refers to a process of treating the metal base with a plasma generated in an atmosphere filled with a mixed gas mainly composed of a major gas and a reactive gas.

In the conventional method, the metal base having machined surfaces obtained by machining as described above has been treated in a plasma generated in an atmosphere filled with the major gas. The inventors, however, found that the edged tool obtained after such plasma treatment was not so sharp.

After our thorough investigations, the inventors found that the edge end portion of the machined surfaces of the metal base was formed into a preferable shape, remarkably improved in sharpness, and improved in durability, when treated in a plasma generated in an atmosphere filled with a mixed gas of a major gas and a reactive gas (preferably a specific ratio of reactive gas), rather than with the major gas only. The present invention was achieved based on the finding.

The mixed gas used here contains the major gas and the reactive gas as major components, where the major components account for 70% or more in terms of volume ratio. In other words, the total content of the major gas and the reactive gas in the mixed gas is 70% by volume or more. The total content is preferably 80% by volume or above, more preferably 90% by volume or above, more preferably 95% by volume or above, more preferably 98% by volume or more, and furthermore preferably 99% by volume or more.

The major gas means a rare gas or nitrogen, wherein nitrogen is preferable.

The reactive gas means a gas other than the major gas, wherein oxygen is preferable.

By using nitrogen as the major gas, and by using oxygen as the reactive gas, the machined surface is preferably shaped more suitably, further remarkably improved in cuttability, and improved in durability. It is therefore further preferable to use the mixed gas of nitrogen and air.

The mixed gas containing nitrogen is preferable since it can nitride the machined surface of the metal base to enhance the strength and durability.

Partial pressure of the major gas (MGP) in the mixed gas is preferably 0.01 to 10 Pa, more preferably 0.1 to 5 Pa, more preferably 0.5 to 2.0 Pa, more preferably 0.9 to 1.4 Pa, and furthermore preferably 1.14 Pa or around.

Partial pressure of the reactive gas (AGP) in the mixed gas is preferably 0.001 Pa or above, more preferably 0.001 to 0.08 Pa, more preferably 0.005 to 0.07 Pa, more preferably 0.01 to 0.05 Pa, and furthermore preferably 0.012 Pa or around.

Partial pressure of the major gas (MGP) in the mixed gas is preferably 0.01 to 10 Pa (preferably 0.5 to 2.0 Pa, and more preferably 0.9 to 1.4 Pa), and, partial pressure of the reactive gas (AGP) is preferably 0.001 Pa or above (preferably 0.001 to 0.08 Pa, more preferably 0.005 to 0.07 Pa, and furthermore preferably 0.01 to 0.05 Pa). This is because the machined surface will be more suitably shaped, remarkably improved in cuttability, and additionally improved in durability.

Pressure of the mixed gas used for generating the plasma is preferably 0.1 to 11 Pa, more preferably 0.3 to 2.5 Pa, more preferably 0.5 to 1.5 Pa, and furthermore preferably 1.2 Pa or around.

Ratio (AGP/MGP) of the partial pressure of reactive gas (AGP) and the partial pressure of major gas (MGP) in the mixed gas is preferably 0.001 to 0.1, preferably 0.002 to 0.05, more preferably 0.006 to 0.06, and furthermore preferably 0.053 or around. This is because the machined surface will be more suitably shaped, and remarkably improved in sharpness, and additionally improved in durability.

As described above, it is preferable to use the mixed gas composed of nitrogen and air, wherein the partial pressure of nitrogen in the mixed gas is preferably 0.1 to 10 Pa, more preferably 0.5 to 2.0 Pa, more preferably 0.9 to 1.3 Pa, and furthermore preferably 1.14 Pa or around. On the other hand, the partial pressure of air in the mixed gas is preferably 0.001 to 1 Pa, more preferably 0.01 to 0.3 Pa, more preferably 0.04 to 0.1 Pa, and furthermore preferably 0.06 Pa or around.

Figure 4:
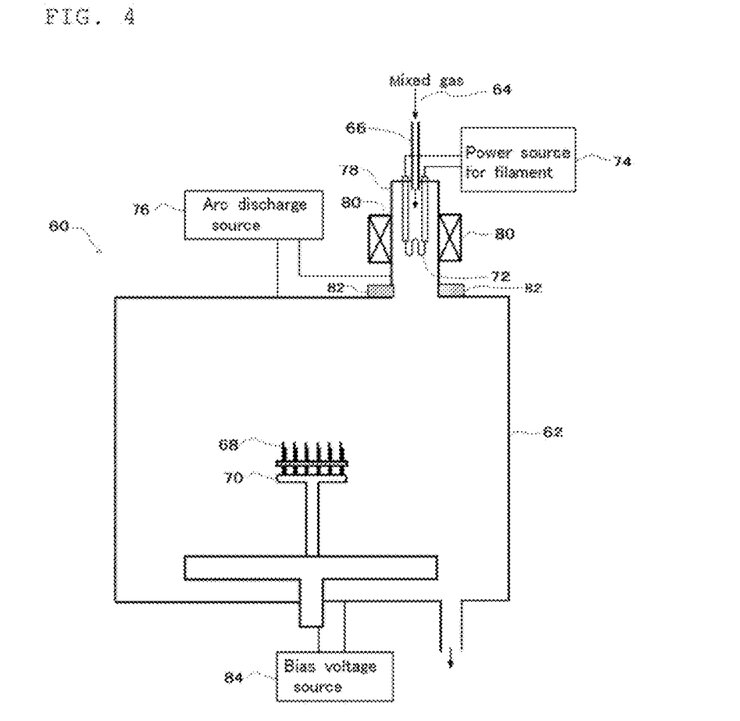
FIG. 4 is a schematic cross sectional view illustrating a plasma device suitable for implementing the method of manufacturing according to the present invention.

The metal base is preferably subjected to plasma treatment using a device illustrated in FIG. 4.

FIG. 4 illustrates a plasma device based on arc discharge using a hot filament. A plasma device 60 illustrated in FIG. 4 has a vacuum chamber 62, a gas feeding unit 66 which introduces a mixed gas 64 into the vacuum chamber 62, a holder 70 which holds a metal base 68 placed in the vacuum chamber 62 and a filament 72 disposed face-to-face therewith, and a power source 74 for filament which feeds current to the filament 72. The plasma device 60 also has a hollow cathode-type electrode 78 which is disposed so as to cover the filament 72 and includes an arc discharge source 76, a coil 80 and an insulator 82 disposed on the outer surface of the hollow cathode-type electrode 78, and a bias voltage source 84 which applies bias voltage to the metal base 68.

In the thus configured plasma device 60, the mixed gas 64 composed of the major gas and the reactive gas is introduced using the gas feeding unit 66 into the vacuum chamber 62 to fill the chamber, and electric current is then fed to the filament 72 so as to trigger glow discharge, to thereby generate a plasma of the mixed gas (discharging gas).

The bias voltage applied herein is preferably 50 to 1000 V, more preferably 300 to 900 V, more preferably 450 to 750 V, and furthermore preferably 600 V or around.

Plasma treatment time is preferably 1 to 10 hours, more preferably 1.5 to 4 hours, and furthermore preferably 2 to 3 hours.

Ion current density is preferably 0.1 to 50 mA/cm$^2$, more preferably 0.5 to 10 mA/cm$^2$, and furthermore preferably 2 to 3 mA/cm$^2$.

The partial pressure of major gas (MGP) and the partial pressure of reactive gas (AGP) in the manufacturing method of this invention are determined, by measuring flow rates of the major gas and the reactive gas, when the mixed gas 64 is fed by the gas feeding unit 66 into the vacuum chamber 62, using flow meters (orifices, etc.), and by calculation based on the obtained measurement values, capacity of the vacuum chamber 62, and volume of gases discharged from the vacuum chamber 62.

For an exemplary case where nitrogen and air are introduced into the vacuum chamber 62, first the individual flow rates are measured using the flow meters similarly as described above, then flow rates of gases corresponded to the major gas and the reactive gas contained in nitrogen and air are calculated based on the individual values of gas concentration, and then the partial pressure values are calculated similarly as described above, additionally using the capacity of the vacuum chamber 62 and the volume of gases discharged from the vacuum chamber 62.

The pressure of the mixed gas is determined as a sum of the partial pressure values of the major gas and the reactive gas measured and calculated as described above.

The edged tool of this invention is successfully obtained by the above described manufacturing method of this invention. The edged tool of this invention is exemplified as illustrated FIG. 5.

Figure 5:
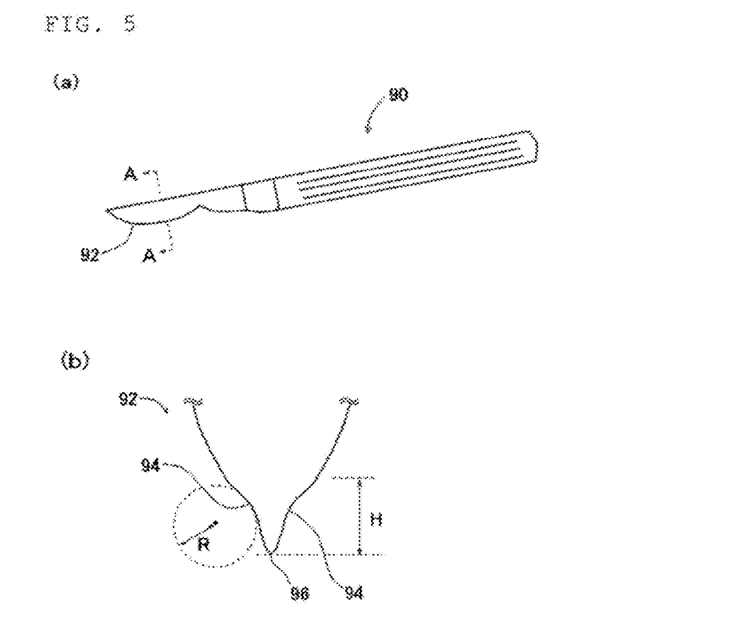
FIG. 5 is a schematic drawing for explaining an edged tool of the present invention.

FIG. 5(a) is a schematic side elevation of a scalpel used for surgical operation, representing a preferable embodiment of the edged tool of this invention, and FIG. 5(b) is a cross sectional view (schematic drawing) taken along line A-A in FIG. 5(a).

An edge end part 92 of a scalpel 90 illustrated in FIG. 5(a) has, as illustrated in FIG. 5(b), two concave surfaces 94 with a predetermined radius of curvature, which cave inwardly in a cross section. The concave surfaces 94 are formed within range H which originates from the edge end 96 towards the spine.

The radius of curvature (R in FIG. 5) of each concave surface is preferably 30 to 2500 nm, and more preferably 100 to 1000 nm.

The range H is preferably 5 to 300 nm, and more preferably 10 to 100 nm.

The thus configured scalpel 90 is extremely sharpened in the edge end 96 by the plasma treatment, and therefore has good cuttability.

EXAMPLE

Example 1

A blade base, which was machined into a shape of surgical blade and composed of a material equivalent to SUS420J2 (Cc 0.6% by mass), was set on the holder mounted on the plasma generating apparatus configured as illustrated in FIG. 4, and the machined surfaces of the edge end were subjected to plasma treatment. The plasma treatment was conducted using a PINK-type plasma device based on arc discharge using a hot filament manufactured by Nagata Seiki Co., Ltd., and using a mixed gas of nitrogen and air (partial pressure of nitrogen=1.14 Pa, partial pressure of air=0.06 Pa, to be introduced into the vacuum chamber), under conditions of an ion current of 2.5 mA/cm$^2$, and a bias voltage of 600 V, for 2 hours.

Figure 6:
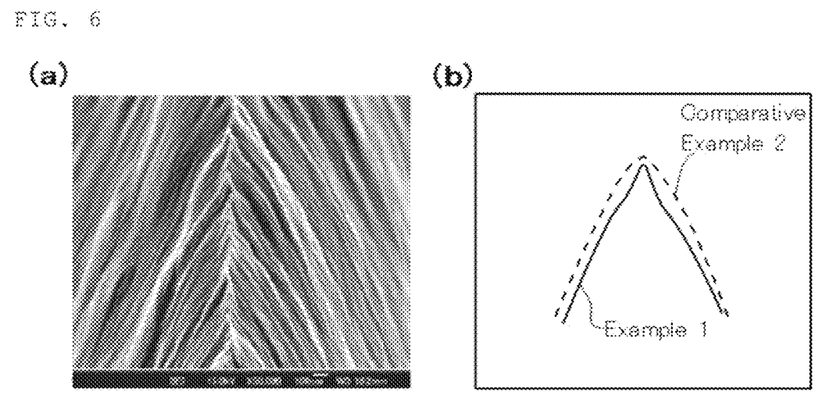
FIG. 6 is an image (enlarged photograph) of an edge obtained in Example 1, observed under a scanning electron microscope (SEM).

The edge end after the plasma treatment was observed under a scanning electron microscope (SEM). An obtained enlarged, photograph (50000× magnification) is shown in FIG. 6. On FIG. 6, the radius of curvature (R) of the concave surfaces formed at the edge end part and the range (H) originated from the edge end were measured.

Note that FIG. 6(a) is an enlarged photograph, and FIG. 6(b) is a transcribed image of a cross section of the edge end, also comparatively showing a dotted line representing Comparative Example 2 which will be described later.

Conditions for treatment are summarized in Table 1, and results of measurement of shape of edge end are summarized in Table 2.

The thus obtained edged tools were also evaluated by cuttability test.

In the cuttability test, pig tongue embedded in paraffin was cut into 2-μm slices using a ball-bearing microtome (from Yamato Kohki Industrial Co., Ltd.), wherein the cuttability was evaluated by the number of slices correctly cut.

Test results of evaluation of cuttability are summarized in Table 3.

Example 2

While the partial pressure of nitrogen and the partial pressure of air, to be introduced into the vacuum chamber in Example 1, were set to 1.14 Pa and 0.06 Pa respectively, now the partial pressure of nitrogen and the partial pressure of air to be introduced into the vacuum chamber in Example 2 were set to 1.14 Pa and 0.005 Pa respectively. All other conditions for the plasma treatment were remained unchanged from those in Example 1.

Conditions for the treatment are summarized in Table 1.

Example 3

While the partial pressure of nitrogen and the partial pressure of air, to be introduced into the vacuum chamber in Example 1, were set to 1.14 Pa and 0.06 Pa respectively, now the partial pressure of nitrogen and the partial pressure of air to be introduced into the vacuum chamber in Example 3 were set to 1.14 Pa and 0.40 Pa respectively. All other conditions for the plasma treatment were remained unchanged from those in Example 1.

Conditions for the treatment are summarized in Table 1.

Comparative Example 1

While the partial pressure of nitrogen and the partial pressure of air in the mixed gas in Example 1 were set to 1.14 Pa and 0.06 Pa respectively, now the mixed gas in Comparative Example 1 was changed to nitrogen (100% by volume). All other conditions for the plasma treatment were remained unchanged from those in Example 1.

Figure 7:
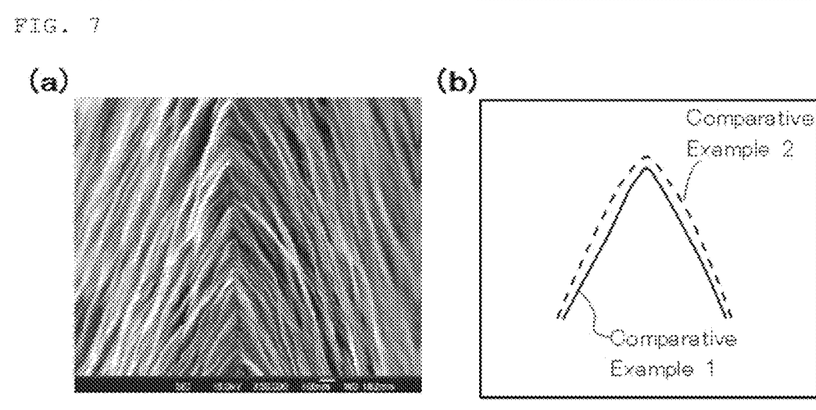
FIG. 7 is an image (enlarged photograph) of an edge obtained in Comparative Example 1, observed under a scanning electron microscope (SEM).

Similarly to Example 1, the edge end after the plasma treatment was observed under a scanning electron microscope (SEM). An obtained enlarged photograph and a transcribed image are shown in FIGS. 7(a) and (b), respectively.

Conditions for the treatment are summarized in Table 1, and results of measurement of shape of edge end are summarized in Table 2.

Also the test for evaluating cuttability was conducted similarly to Example 1. Test results of evaluation of cuttability are summarized in Table 3.

Comparative Example 2

A surgical blade composed of a material equivalent to SUS420J2 (C: 0.6% by mass) was obtained by machining similarly to Example 1.

Figure 8:
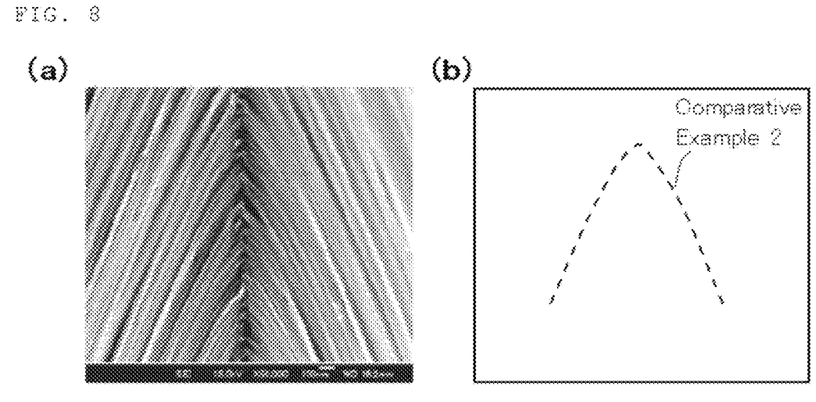
FIG. 8 is an image (enlarged photograph) of an edge obtained in Comparative Example 2, observed under a scanning electron microscope (SEM).

Again similarly to Example 1, the edge end was observed under a scanning electron microscope (SEM). An obtained enlarged photograph and an transcribed image are shown in FIGS. 8(a) and (b), respectively.

Results of measurement of shape of edge end are summarized in Table 2.

Also the test for evaluating cuttability was conducted similarly to Example 1. Test results of evaluation of cuttability are summarized in Table 3.

TABLE 1

| | Example 1 | Example 2 | Example 3 | Comparative Example 1 |
|---|---|---|---|---|
| Case description | Plasma of nitrogen added with air | Plasma of nitrogen added with air | Plasma of nitrogen added with air | Plasma of nitrogen only |
| Material | SUS420 | SUS420 | SUS420 | SUS420 |
| Pressure of introduced air [Pa] | 0.06 | 0.005 | 0.40 | Not detected |
| Pressure of introduced nitrogen [Pa] | 1.14 | 1.14 | 1.14 | 1.14 |
| Pressure of mixed gas [Pa] | 1.20 | 1.15 | 1.54 | 1.14 |
| Pressure of oxygen in mixed gas | 0.013 | 0.001 | 0.084 | — |

TABLE 1-continued

|  | Example 1 | Example 2 | Example 3 | Comparative Example 1 |
|---|---|---|---|---|
| (calculated value, Pa) Pressure of nitrogen in mixed gas (calculated value, Pa) | 1.19 | 1.14 | 1.46 | 1.14 |
| Ion current density [mA/cm$^3$] | 2.5 | 2.5 | 2.5 | 2.5 |
| Bias voltage value [V] | 600 | 600 | 600 | 600 |
| Treatment time [Hr] | 2 | 2 | 2 | 2 |
| AGP/MGP (calculated value) | 0.011 | 0.001 | 0.058 | 0 |

TABLE 2

|  | Example 1 | Comparative Example 1 | Comparative Example 2 |
|---|---|---|---|
| Radius of curvature (R, nm) | 500 nm | Infinite | Infinite |
| Range H (nm) | 80 nm | — | — |

TABLE 3

|  | Example 1 | Comparative Example 1 | Comparative Example 2 |
|---|---|---|---|
| Number of correct slices | 43 | 23 | 26 |

It is understood from comparison among FIG. 6 to FIG. 8, that the edge is most sharpened in the case illustrated in FIG. 6. XRD analysis revealed that almost same levels of state of generation of intermetallic compounds (Fe$_4$N, Cr$_4$N) were observed in the cases illustrated in FIG. 6 and FIG. 7. Measurement using a micro Vickers hardness meter revealed almost same levels of hardness in the cases illustrated in FIG. 6 and FIG. 7.

The edge ends obtained in Example 2 and Example 3 were found to be sharper than the edge end obtained in Comparative Example 1. It is therefore considered, from comparison with the edge end of Comparative Example 1, that the edge ends obtained in Examples 2 and 3 have good cuttability.

Note, however, that the edge end obtained in Example 1 was found to have cuttability further superior to that of the edge ends obtained in Examples 2 and 3. It is therefore concluded that the edge end obtained in Example 1 is more preferable than the edge ends obtained in Examples 2 and 3.

It was also confirmed, from the test results of evaluation of cuttability summarized in Table 3, that the edged tool of Example 1 showed the best cuttability. The edged tool of Comparative Example 1 was found to be further duller than the edged tool of Comparative Example 2, since the edge end was formed to have an obtuse angle.

REFERENCE SIGNS LIST 1, 11 blade base
3, 13 edge end
5, 15, 34 back end
17, 52 machined surface
19 first boundary
21, 56 apical surface
23 second boundary
25, 32 side face
30 blade-forming member
36 belly-side end
38, 46 apical ground surface
40 edge end
42, 50 ground side face
44, 48, 54 boundary
α predetermined sharpening angle
β predetermined apical angle
T thickness
X thickness direction
60 plasma device
62 vacuum chamber
64 mixed gas
66 gas feeding unit
68 metal base
70 holder
72 filament
74 power source for filament
76 arc discharge source
78 hollow cathode-type electrode
80 coil
82 insulator
84 bias voltage source
90 scalpel
92 edge end part
94 concave surface
96 edge end
R radius of curvature
H range

The invention claimed is:

1. A method of manufacturing an edged tool, the method comprising:
   manufacturing an edge tool by machining a metal base, and
   treating the metal base, having a machined surface obtained by machining, with a plasma generated in a vacuum chamber filled with a mixed gas mainly composed of nitrogen as a major gas and oxygen as a reactive gas, wherein
   the metal base is a blade base formed by machining a plate-like blade forming member at a belly-side end from both sides in a thickness direction, so as to give two machined surfaces which come apart in a direction from an edge towards a spine, while forming in between a predetermined sharpening angle,
   in the treating the metal base, forming the machined surface therein a concave surface, with 30 to 2500 nm radius of curvature, which caves inwardly within range (H) of 5 to 300 nm originated from the edge towards the spine, the step being performed by treating with plasma, and
   the concave surface is formed on each of the two machined surfaces.

2. The method of manufacturing an edged tool of claim 1, wherein a ratio (AGP/MGP) of partial pressure of reactive gas (AGP) and partial pressure of major gas (MGP) in the mixed gas is 0.001 to 0.1.

3. The method of manufacturing an edged tool of claim 1, wherein a partial pressure of major gas (MGP) in the mixed gas is 0.01 to 10 Pa, and a partial pressure of reactive gas (AGP) is 0.001 Pa or higher.

4. A plasma device suitable for implementing the manufacturing method described in claim 1, the plasma device comprising the vacuum chamber, a gas feeding unit which introduces the mixed gas into the vacuum chamber, a holder which holds the metal base placed in the vacuum chamber and a filament disposed face-to-face therewith, and a power source for filament which feeds current to the filament.

* * * * *